(12) United States Patent
Fristrup et al.

(10) Patent No.: US 10,696,626 B2
(45) Date of Patent: Jun. 30, 2020

(54) PHOTOINITATORS

(71) Applicant: Coloplast A/S, Humlebaek (DK)

(72) Inventors: Charlotte Juel Fristrup, Virum (DK); Petr Sehnal, York (GB); Bahar Bingol, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 16/462,940

(22) PCT Filed: Nov. 21, 2017

(86) PCT No.: PCT/DK2017/050385
§ 371 (c)(1),
(2) Date: May 22, 2019

(87) PCT Pub. No.: WO2018/095495
PCT Pub. Date: May 31, 2018

(65) Prior Publication Data
US 2019/0308935 A1    Oct. 10, 2019

(30) Foreign Application Priority Data

Nov. 22, 2016 (DK) .............................. 2016 70929

(51) Int. Cl.
| | | |
|---|---|---|
| C07C 317/28 | (2006.01) | |
| C08F 2/50 | (2006.01) | |
| C07C 235/82 | (2006.01) | |
| C07C 69/757 | (2006.01) | |
| C07C 311/10 | (2006.01) | |
| C07C 49/517 | (2006.01) | |

(52) U.S. Cl.
CPC .......... *C07C 317/28* (2013.01); *C07C 49/517* (2013.01); *C07C 69/757* (2013.01); *C07C 235/82* (2013.01); *C07C 311/10* (2013.01); *C08F 2/50* (2013.01); *C07C 2602/42* (2017.05)

(58) Field of Classification Search
None
See application file for complete search history.

(56) References Cited

U.S. PATENT DOCUMENTS

| | | | | |
|---|---|---|---|---|
| 5,607,985 A | * | 3/1997 | Masuhara | ................. C08F 2/50 156/327 |
| 7,803,850 B2 | * | 9/2010 | Ikemura | ................. A61K 6/887 522/47 |

FOREIGN PATENT DOCUMENTS

| | | |
|---|---|---|
| WO | 2000033826 A1 | 6/2000 |
| WO | 2012062332 A2 | 5/2012 |

OTHER PUBLICATIONS

Pande et al. "Camphorquinone-10-sulfonic acid and derivatives: Convenient reagents for reversible modification of arginine residues", Proc. Natl. Acad. Sci. USA, Feb. 1980, vol. 77, No. 2, pp. 895-899.

Kamoun et al.. "Carboxylated camphorquinone as visible-light photoinitiator for biomedical application: Synthesis, characterization, and application", Arabian Journal of Chemistry, Mar. 2014, pp. 1-10.

Temel et al.. "Photopolymerization and photophysical properties of amine linked benzophenone photoinitiator for free radical polymerization", Journal of Photochemistry and Photobiology A: Chemistry, 2011, vol. 219, pp. 26-31.

\* cited by examiner

*Primary Examiner* — Amy C Bonaparte
(74) *Attorney, Agent, or Firm* — Coloplast Corp., Coloplast A/S; Nick Baumann

(57) ABSTRACT

A photoinitiator is provided which incorporates a camphorquinone photoinitiator moiety.

21 Claims, No Drawings

PHOTOINITATORS

BACKGROUND

Curing organic materials can be accomplished, e.g., by irradiation with ultraviolet or visible light. Achieving a proper irradiation curing requires efficient methods of initiating the chemical reaction responsible for the curing process. Photoinitiators may be used to effect curing of organic materials through generation of radical species upon irradiation with, e.g., UV light.

For materials used in the medical field, patient safety considerations limit the amount and type of substance which can leach (=be released) from a given material.

There is a need for photoinitiators in which leaching of small molecules may be reduced or even eliminated. Additional important considerations include the curing time of the material to be cured, the curing method and the compatibility of the photoinitiator with other components of said material.

SUMMARY

A photoinitiator is thus provided which incorporates a camphorquinone photoinitiator moiety, i.e. a photoinitiator of the formula (I)

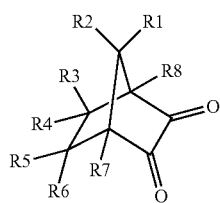

in which R3, R4, R5 and R6 are selected from H or $C_1$-$C_6$ alkyl;
wherein one of R1, R2, R7 or R8 has a structure of formula (Ia):

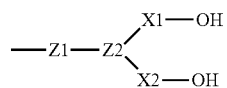

in which:
Z1 is a linker comprising one or more linker units selected from a single bond, —O—, —S—, optionally-substituted —($C_1$-$C_{12}$ alkylene)-, optionally-substituted —($C_1$-$C_{12}$ alkenylene)-, —$SO_2$—, —CO—, —NR'—, —Si(R')$_2$—, optionally-substituted heterocyclyl and optionally-substituted aryl in which R' is H or $C_1$-$C_6$ alkyl;
wherein linker —Z1-, optionally in combination with —Z2-, comprises at least one sulfonamide, a sulfonic ester, a carboxamide or a carboxylate ester moiety;
Z2 is a trivalent nitrogen atom or Z2 is C(R"), in which R" is H or $C_1$-$C_6$ alkyl; provided that—when Z2 is a nitrogen atom—the linker unit in Z1 adjacent to Z2 is —$SO_2$— or —CO—;
each of X1 and X2 are independently selected from a single bond, or a linker comprising one or more linker units selected from —O—, —S—, optionally-substituted —($C_1$-$C_{12}$ alkylene)-, optionally-substituted —($C_1$-$C_{12}$ alkenylene)-, —$SO_2$—, —CO—, —NR'—, optionally-substituted heterocyclyl and optionally-substituted aryl in which R' is H or $C_1$-$C_6$ alkyl;
and wherein X1 and X2 may be linked to one another or to Z1 to form one or more ring structures;
and wherein the remaining R1, R2, R7 and R8 are selected from H or $C_1$-$C_6$ alkyl.

Further aspects of the invention are presented in the following specification and the dependent claims.

DETAILED DISCLOSURE

Definitions

In the following, when a part of a molecule is described as "optionally substituted" it is meant that said part may be substituted by one or more substituents selected from: $C_1$-$C_6$ linear, branched or cyclic alkyl, aryl, —OH, —CN, —$NO_2$, halogens, amines, amides, alcohols, ethers, thioethers, sulfones and derivatives thereof, sulfoxides and derivatives thereof, carbonates, isocyanates, nitrates and acrylates. Preferable substituents are $C_1$-$C_6$ linear alkyl, —OH, halogens, amines and alcohols.

The term "heterocyclyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom, respectively, is present as a ring atom. The heterocyclyl can be optionally substituted as described above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

The term "alkylene" is used in the following to specify moieties derived from alkanes in which two H atoms have been removed to form a diradical species. The simplest alkylene is methylene —$CH_2$—, and other alkylenes include ethylene —$CH_2$—$CH_2$—, propylene —$C_3H_6$— and butylene —$C_4H_8$—. The term "alkylene" includes branched, linear and cyclic alkylenes, with linear alkylenes being most preferred. An alkylene which is a $C_1$-$C_{12}$ alkylene is one which contains between 1 and 12 carbon atoms. Preferred alkylenes contain between 1 and 6 carbon atoms (i.e. $C_1$-$C_6$ alkylenes).

The term "alkenylene" is used in the following to specify moieties derived from alkenes in which two H atoms have been removed to form a diradical species. Examples include ethenylene —$CH_2$=$CH_2$— and propenylene —$C_3H_4$— moieties. The term "alkenylene" includes branched, linear and cyclic alkenylene, with linear alkenylene being most preferred.

The term "aryl" is used to define an unsaturated cyclic system which contains a delocalised π-electron system about the ring. Aryl groups may comprise from 4-12 atoms, suitably from 6-8 atoms, most suitably 6 atoms. "Aryl" preferably comprises carbocyclic rings, and is preferably phenyl (—$C_6H_5$).

The term "aryl" in the present invention is also used to include aromatic heterocycles, i.e. rings in which one or more atoms in the ring (e.g. 1-3 atoms) are N, S, P or O.

Aromatic heterocycles include pyrrole, furan, thiophene, imidazole, imidazoline, pyrazole, pyrazoline, oxazole, oxazoline, isoxazole, isoxazoline, thiazole, thiazoline, isothiazole, isothiazoline (5-membered rings), pyridine, pyran, thiopyran (6-membered rings). The term "aryl" also includes fused ring systems.

When referring to a linker (e.g. Z, X1, X2), the term "aryl" is used to define moieties derived from arenes in which two H atoms have been removed to form a diradical species (i.e. arylene). Examples include 1,2-phenylene, 1,3-phenylene and 1,4-phenylene.

In one aspect, a photoinitiator is provided which incorporates a camphorquinone photoinitiator moiety.

The camphorquinone moieties are efficient in transforming light from a visible light source to reactive radicals which can abstract hydrogen atoms and other labile atoms and hence effect cross-linking.

Radical photoinitiator moieties can be classified as either cleavable (Norrish type I reaction) or non-cleavable (of which the Norrish type II reaction is a special case, see e.g. A. Gilbert, J. Baggott: "Essentials of Molecular Photochemistry", Blackwell, London, 1991). Upon excitation, cleavable photoinitiator moieties spontaneously break down into two radicals, at least one of which is reactive enough to abstract a hydrogen atom from most substrates.

Camphorquinone is an example of a cleavable photoinitiator moiety (Type-I). Addition of electron donors (such as amines) to such systems is not required but may enhance the overall efficiency of cleavable photoinitiator moieties.

The photoinitiator has the general formula (I):

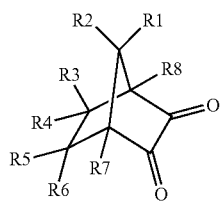

(I)

In formula (I), R3, R4, R5 and R6 are selected from H or $C_1$-$C_6$ alkyl. Suitably, R3, R4, R5 and R6 are selected from H or methyl, more preferably H.

In formula (I), one of R1, R2, R7 or R8 has a structure of formula (Ia):

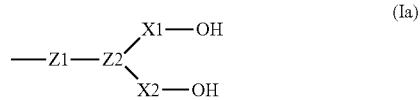

(Ia)

While the remaining R1, R2, R7 and R8 are selected from H or $C_1$-$C_6$ alkyl. Furthermore, R1 and R2 may both be methyl.

Suitably, it is R2, R7 or R8, preferably R7 or R8, which has a structure of formula (Ia).

In Formula (Ia), Z1 is a linker comprising one or more linker units selected from a single bond, —O—, —S—, optionally-substituted —($C_1$-$C_{12}$ alkylene)-, optionally-substituted —($C_1$-$C_{12}$ alkenylene)-, —$SO_2$—, —CO— —NR'—, —Si(R')$_2$—, optionally-substituted heterocyclyl and optionally-substituted aryl in which R' is H or $C_1$-$C_6$ alkyl. Suitably, at least one linker unit in Z1 is selected from —$SO_2$—, —O— or —CO—, preferably —$SO_2$— or —CO—.

Linker —Z1-, optionally in combination with —Z2-, comprises at least one sulfonamide, a sulfonic ester, a carboxamide or a carboxylate ester moiety. This moiety forms part of the linker structure itself, rather than being part of a side chain or a pendant moiety.

In Formula (Ia), Z2 is a trivalent nitrogen atom or Z2 is C(R"), in which R" is H or $C_1$-$C_6$ alkyl; provided that— when Z2 is a nitrogen atom—the linker unit in Z1 adjacent to Z2 is —$SO_2$— or —CO—.

Suitable structures for —Z1-Z2- may be selected from the group comprising;
—$SO_2$—N—;
—CO—N—;
—CO—O—CR"—;
—O—CO—CR"—;
—($C_1$-$C_{12}$ alkylene)-$SO_2$—N—;
—($C_1$-$C_{12}$ alkylene)-CO—N—;
—($C_1$-$C_{12}$ alkylene)-CO—O—CR"—;
—($C_1$-$C_{12}$ alkylene)-O—CO—CR"—,
—($C_1$-$C_{12}$ alkylene)-$SO_2$—O—($C_1$-$C_{12}$ alkylene)-Z2-;
—($C_1$-$C_{12}$ alkylene)-$SO_2$—NR'—($C_1$-$C_{12}$ alkylene)-Z2-;
—($C_1$-$C_{12}$ alkylene)-O—$SO_2$—($C_1$-$C_{12}$ alkylene)-Z2-;
—($C_1$-$C_{12}$ alkylene)-NR'—$SO_2$—($C_1$-$C_{12}$ alkylene)-Z2-;
—($C_1$-$C_{12}$ alkylene)-CO—O—($C_1$-$C_{12}$ alkylene)-Z2-;
—($C_1$-$C_{12}$ alkylene)-O—CO—($C_1$-$C_{12}$ alkylene)-Z2-;
—($C_1$-$C_{12}$ alkylene)-CO—NR'—($C_1$-$C_{12}$ alkylene)-Z2-; or
—($C_1$-$C_{12}$ alkylene)-NR'—CO—($C_1$-$C_{12}$ alkylene)-Z2-;
preferably from
—$SO_2$—N—;
—CO—N—;
—CO—O—CR"—;
—O—CO—CR";
—($C_1$-$C_{12}$ alkylene)-$SO_2$—N—;
—($C_1$-$C_{12}$ alkylene)-CO—N—;
—($C_1$-$C_{12}$ alkylene)-CO—O—CR"—;
—($C_1$-$C_{12}$ alkylene)-O—CO—CR"—;
—($C_1$-$C_{12}$ alkylene)-$SO_2$—O—($C_1$-$C_{12}$ alkylene)-Z2-;
—($C_1$-$C_{12}$ alkylene)-$SO_2$—NR'—($C_1$-$C_{12}$ alkylene)-Z2-;
—($C_1$-$C_{12}$ alkylene)-CO—O—($C_1$-$C_{12}$ alkylene)-Z2-;
—($C_1$-$C_{12}$ alkylene)-CO—NR'—($C_1$-$C_{12}$ alkylene)-Z2-; or
more preferably from
—$SO_2$—N—;
—CO—N—;
—($C_1$-$C_{12}$ alkylene)-$SO_2$—N—;
—($C_1$-$C_{12}$ alkylene)-CO—N—;
—($C_1$-$C_{12}$ alkylene)-$SO_2$—O—($C_1$-$C_{12}$ alkylene)-Z2-; or
—($C_1$-$C_{12}$ alkylene)-CO—O—($C_1$-$C_{12}$ alkylene)-Z2-.

In one aspect, Z2 is N. In another aspect, Z2 is C(R"), in which R" is H, methyl or ethyl or propyl. In a further aspect, the —($C_1$-$C_{12}$ alkylene)- linker unit in Z1 is —($C_1$-$C_6$ alkylene)-, such as propylene, ethylene or methylene.

Suitably, the linker Z1 has a molecular weight of less than 10000 Da, suitably less than 5000 Da, most suitably less than 1000 Da. The linker Z1 preferably comprises no more than 50 atoms, preferably no more than 30 atoms.

In Formula (Ia), each of X1 and X2 are independently selected from a single bond, or a linker comprising one or more linker units selected from —O—, —S—, optionally-substituted —($C_1$-$C_{12}$ alkylene)-, optionally-substituted —($C_1$-$C_{12}$ alkenylene)-, —$SO_2$—, —CO—, —NR'—, optionally-substituted heterocyclyl and optionally-substituted aryl in which R' is H or $C_1$-$C_6$ alkyl; and X1 and X2 may be linked to one another or to Z1 to form one or more ring structures.

In one aspect, X1 and X2 are independent linkers comprising one or more linker units selected from —O—, —S—, optionally-substituted —($C_1$-$C_{12}$ alkylene)-, —$SO_2$—, —CO—, and —NR'— in which R' is H or $C_1$-$C_6$ alkyl; preferably one or more linker units selected from —O—, —S—, and optionally-substituted —($C_1$-$C_{12}$ alkylene)-. The —($C_1$-$C_{12}$ alkylene)- linker unit in X1 and X2 may be —($C_1$-$C_6$ alkylene)-, such as propylene, ethylene or methylene. In a preferred aspect, X1 and X2 are independently —($C_1$-$C_{12}$ alkylene)-; preferably —($C_1$-$C_6$ alkylene)-, such as propylene, ethylene or methylene. Suitably, X1 and X2 are the same.

In particular aspects, one of R1, R2, R3, R4, R5, R6, R7 or R8 is selected from the group consisting of:

Particular photoinitiators may be selected from the group comprising:

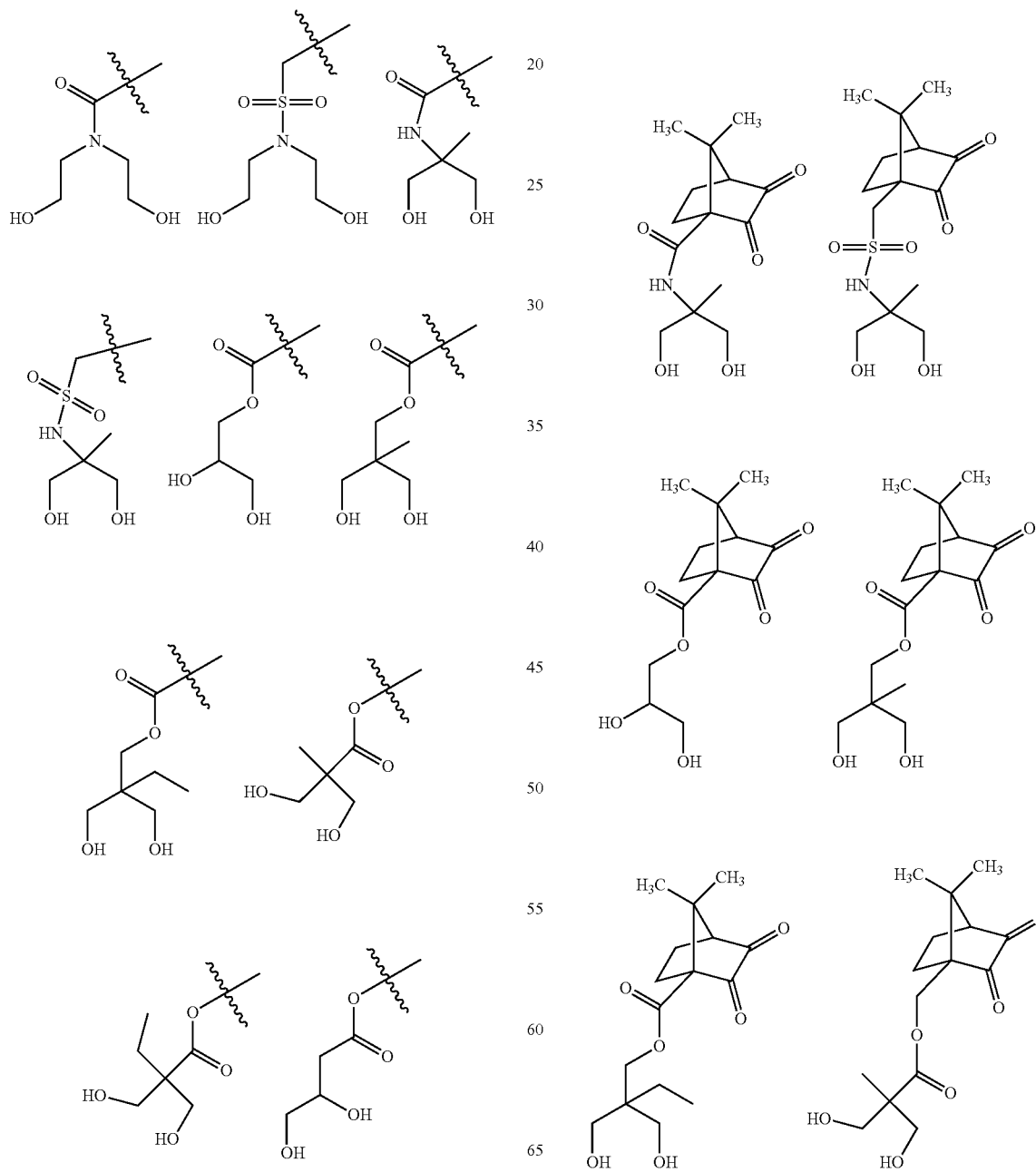

-continued

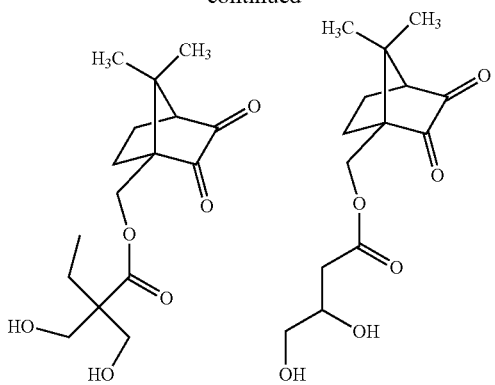

EXAMPLES

Experimental Procedures

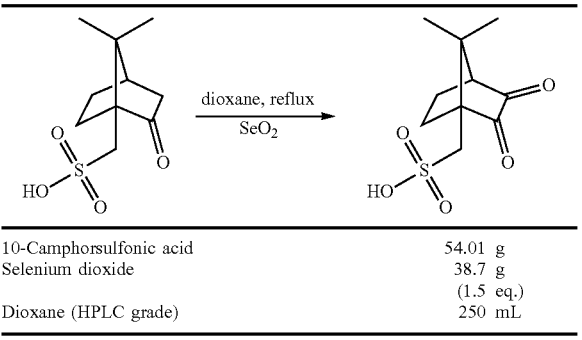

| 10-Camphorsulfonic acid | 54.01 g |
| Selenium dioxide | 38.7 g |
| | (1.5 eq.) |
| Dioxane (HPLC grade) | 250 mL |

Solid 10-camphorsulfonic acid was suspended in the dioxane solvent and the stirred mixture was refluxed for 120 hours (temperature was reduced from reflux to 60° C. overnight). An intense bright yellow solution and black solid were obtained. The grey/black solid was filtered off and the clear yellow solution was evaporated to a thick oily residue. The residue was dissolved in water (200 mL), acidified with 40 mL water+20 mL 37% HCl. To the stirred slightly turbid yellow/orange solution was added overnight: 30 g sodium bisulfite ($Na_2S_2O_5$/$NaHSO_3$) in 100 mL water. A turbid red-brown suspension was obtained. The suspension was warmed to 80° C. for 1 h to convert the selenium into a black filterable form. The metallic selenium was filtered off and the aqueous filtrate was evaporated to an oil, which completely solidifies in the fridge overnight. The bright yellow solid was extracted with methanol (250 mL). The white inorganics were filtered off and the bright yellow filtrate evaporated to dryness. The yellow solid shows very good purity on NMR. Further inorganic residues were removed by suspending the solid in warm tetrahydrofuran (1000 mL) and filtering. This provides a bright yellow solution which is evaporated to dryness to provide 10-camphorquinone sulfonic acid (45.8 g; 80% yield).

$^1$H NMR (400 MHz, DMSO-$d_6$): 3.01 (d, J=14.6 Hz, 1H), 2.73 (m, 1H), 2.72 (d, J=14.6 Hz, 1H), 2.61 (d, J=5.3 Hz, 1H), 2.15 (m, 1H), 1.70 (m, 1H), 1.51 (m, 1H), 1.11 (s, 3H), 0.83 (s, 3H).

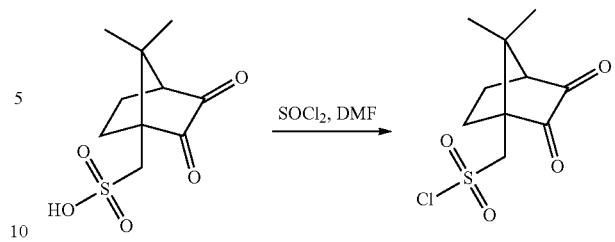

Synthesis of the camphorquinone-10-sulfonyl chloride is described in: C. S. Pande, M. Pelzig, J. D. Glass, Proc. Natl. Acad. Sci. USA, Vol. 77, No. 2, pp. 895-899, February 1980.
A modified procedure was carried out as follows:
60 mL thionyl chloride was added dropwise over 20 min into 100 mL cold DMF (ice/water cooled).
The solution was stirred for 30 min at 0° C.
Camphorquinone-10-sulfonic acid (42 g) was added into the very pale yellow solution as a solid over 30 min.
The yellow-brown reaction mixture was stirred at ambient temperature for 3 h.
The lightly turbid yellow-brown reaction mixture was added dropwise into a rapidly stirred mixture of ice (800 g) and water (400 mL).
The precipitated sand-yellow solid was filtered off rapidly at 0° C. (fairly pale yellow liquor) and allowed to dry under high vacuum at ambient temperature. A sand-yellow powder product was obtained. m=314.1−280.5=33.6 g (74%).
The product was stored in the freezer and reacted further within 10 days.

$^1$H NMR (400 MHz, CDCl$_3$): 4.36 (d, J=14.7 Hz, 1H), 3.89 (d, J=14.7 Hz, 1H), 2.74 (d, J=5.3 Hz, 1H), 2.70-2.63 (m, 1H), 2.38-2.29 (m, 1H), 2.08-2.01 (m, 1H), 1.81-1.74 (m, 1H), 1.24 (s, 3H), 1.02 (s, 3H).

$^{13}$C NMR (100 MHz, CDCl$_3$): 198.91, 198.74, 77.16, 62.86, 59.59, 57.41, 44.52, 25.56, 22.00, 20.97, 18.24.

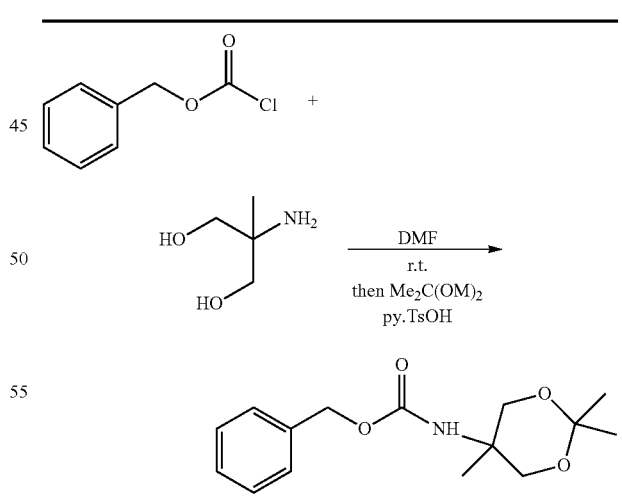

Literature reference: J. Nat. Prod. 1999, 62, 963-968.

| 2-amino-2-methylpropane-1,3-diol | 16.5849 g |
| DMF (anhydrous) | 104 mL |

The 2-amino-2-methylpropane-1,3-diol was dissolved in dry DMF with stirring. Benzyl chloroformate (23.7 mL) was added dropwise over approximately 20 min with ice/water cooling. A strong exotherm is observed and HCl gas is released. The colourless reaction mixture was stirred at ambient temperature overnight under calcium chloride moisture exclusion. To the colourless clear solution was added 2,2-dimethoxypropane (45 mL) and pyridinium p-toluene sulfonate (1.24 g) and stirred at ambient temperature for 48 h. The reaction mixture was slowly added into a solution of sodium bicarbonate (40 g) in water/ice (800 mL). Purity of the product was checked by TLC (AcOEt 100%). The aqueous phase was extracted again with AcOEt (2×200 mL), the organic phase was re-extracted with water to remove the starting aminodiol, dried and evaporated to dryness. The oily residue was dried at 70° C. in vacuo to remove most of the benzyl chloride by-product. The oil partially crystallizes in the fridge over 60 h. Hexane (50 mL) was added to complete the solidification of the product, the colourless crystals were filtered off and washed with hexane (100 mL). The product was dried by passing air through at ambient on the sinter. This provides the desired product benzyl (2,2,5-trimethyl-1,3-dioxan-5-yl)carbamate as fine crystalline colourless needles. Yield=16.756 g (38%).

$^1$H NMR (400 MHz, CDCl$_3$): 7.37-7.29 (m, 5H), 5.35 (bs, 1H), 5.07 (s, 2H), 3.90 (d, J=11.7 Hz, 2H), 3.66 (d, J=11.7 Hz, 2H), 1.43 (s, 3H), 1.42 (s, 3H), 1.28 (s, 3H).

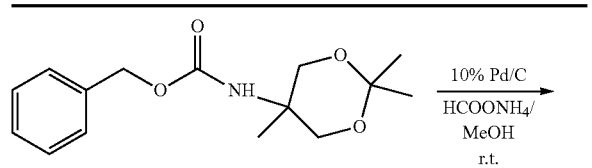

| | |
|---|---|
| Benzyl (2,2,5-trimethyl-1,3-dioxan-5-yl)carbamate from previous step | 16.756 g |
| Ammonium formate | 19.1 g |
| Methanol (HPLC) | 250 mL |
| Palladium on carbon (10%) | 1.75 g |

The solid benzyl (2,2,5-trimethyl-1,3-dioxan-5-yl)carbamate was added into methanol (most of the solid is not dissolved), then Pd/C was added. With rapid stirring, portions of the solid ammonium formate were added into the reaction mixture under a stream of nitrogen over approximately 30 min (slight evolution of gas, no visible exotherm). The reaction was allowed to stir overnight at ambient temperature. TLC (AcOEt/hexane 3:10) confirms complete disappearance of the starting material. The Pd/C was filtered off, washed with methanol and the colourless filtrate was evaporated to dryness. The oil obtained quickly solidifies. The solid was redissolved in water (150 mL), the pH was adjusted to 13 with NaOH and the solution was saturated with sodium sulfate. The mixture was extracted with ethyl acetate (5×100 mL). Evaporation provides 2,2,5-trimethyl-1,3-dioxan-5-amine as a colourless liquid. m=7.2 g (83% yield).

$^1$H NMR (400 MHz, CDCl$_3$): 3.74 (d, J=11.5 Hz, 1H), 3.42 (d, J=11.5 Hz, 1H), 1.76 (bs, 2H), 1.44 (s, 3H), 1.43 (s, 3H), 1.00 (s, 3H).

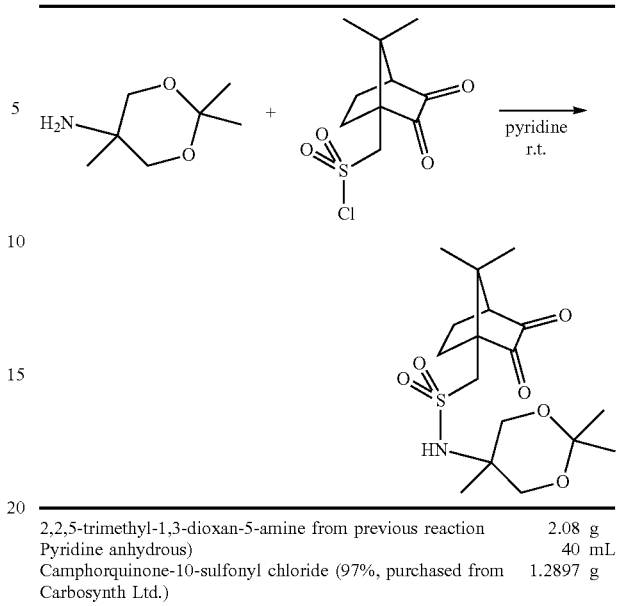

| | |
|---|---|
| 2,2,5-trimethyl-1,3-dioxan-5-amine from previous reaction | 2.08 g |
| Pyridine anhydrous) | 40 mL |
| Camphorquinone-10-sulfonyl chloride (97%, purchased from Carbosynth Ltd.) | 1.2897 g |

The camphorquinone-10-sulfonyl chloride solid was charged into the pyridine solution of 2,2,5-trimethyl-1,3-dioxan-5-amine over 20 min with cooling, then it was allowed to stir overnight at ambient temperature. The bright yellow reaction mixture was diluted with ethyl acetate (100 mL) and extracted with water (3×100 mL). The yellow organic extract was dried and evaporated to provide a bright yellow glassy solid which was used in the next step without further purification.

$^1$H NMR (400 MHz, CDCl$_3$): 5.87 (s, 1H), 3.98 (dd, J=12.5, 2.9 Hz, 1H), 3.87-3.83 (m, 2H), 3.74 (dd, J=12.3, 1.8 Hz, 2H), 3.26 (d, J=14.9 Hz, 1H), 2.68 (d, J=5.1 Hz, 1H), 2.58-2.46 (m, 1H), 2.29-2.18 (m, 2H), 1.75-1.68 (m, 1H), 1.45 (s, 3H), 1.36 (s, 3H), 1.34 (s, 3H), 1.14 (s, 3H), 0.99 (s, 3H).

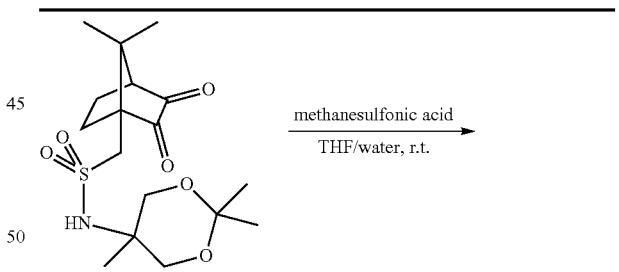

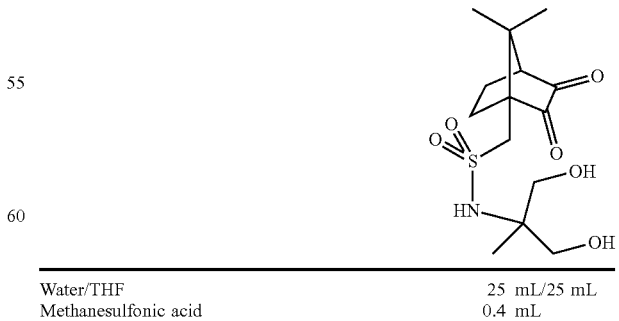

| | |
|---|---|
| Water/THF | 25 mL/25 mL |
| Methanesulfonic acid | 0.4 mL |

The crude material from the previous step was dissolved in the THF/water mixture and the clear bright yellow solution was stirred at ambient temperature with exclusion of light overnight. TLC (AcOEt/DCM 1:5) confirmed the near quantitative conversion to 1 polar product. Sodium bicarbonate (5 g) was added to the reaction mixture in order to neutralise the acid. After stirring for 5 min the reaction mixture was partitioned between water (150 mL) and ethyl acetate (150 mL). The pale yellow aqueous phase (pH 8) was extracted again with ethyl acetate (100 mL), the organic phases were combined, dried ($Na_2SO_4$) and evaporated to dryness. The viscous residue was dissolved in dichloromethane and chromatographed on silica (eluent: AcOEt/DCM 1:10-1:0). The main yellow band was collected and evaporated to dryness. m=0.9 g (55% yield over two steps). This yields the desired product N-(1,3-dihydroxy-2-methylpropan-2-yl)-1-(7,7-dimethyl-2,3-dioxobicyclo[2.2.1]hept-1-yl)methanesulfonamide as a bright yellow glassy material that solidifies on standing.

Melting point (@ 1.0° C./min): 108-117° C.

$^1$H NMR (400 MHz, $CD_3OD$): 0.95 (s, 3H), 1.18 (s, 3H), 1.34 (s, 3H), 1.62-1.69 (m, 1H), 1.92-2.00 (m, 1H), 2.25-2.34 (m, 1H), 2.59-2.67 (m, 2H), 3.44 (d, J=15.0 Hz, 1H), 3.60-3.67 (m, 4H), 3.78 (d, J=15.0 Hz, 1H).

$^{13}$C NMR (100 MHz, $CD_3OD$): 18.17, 19.60, 21.30, 22.88, 26.90, 44.97, 53.00, 58.78, 60.48, 62.28, 66.50, 66.57, 202.27, 202.66.

$E_1{}_{cm}^{1\%}$=1.012 (@ 461 nm in methanol)

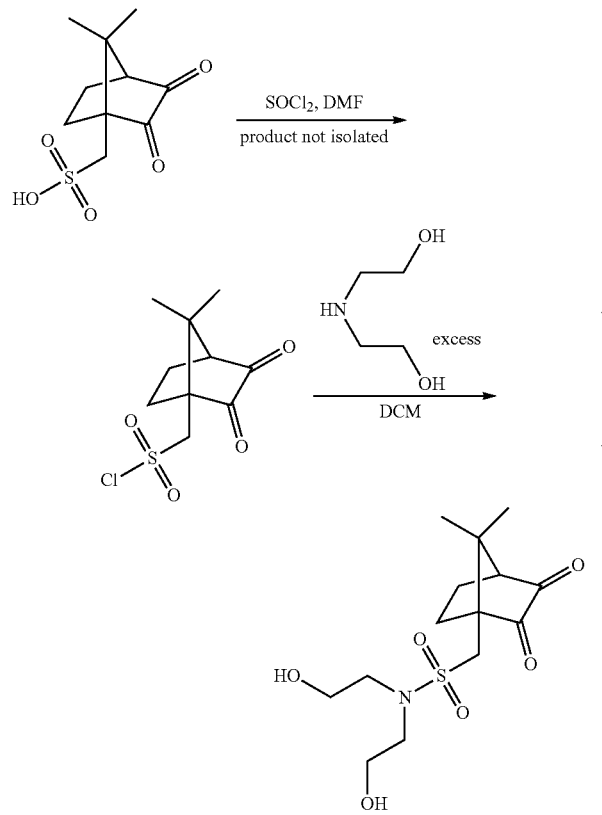

10-camphorquinone sulfonic acid (30 g) was dissolved in anhydrous DMF (100 mL) under nitrogen and the solution was cooled with ice/water. Thionyl chloride (100 mL) was added over 1 hour with ice cooling and exclusion of light. The reaction mixture was stirred at ambient temperature for 16 h and then carefully added dropwise into ice/water (2000 mL) over 30 minutes. The ice-cold suspension was extracted with dichloromethane (2*300 mL), the organic phase was dried and filtered to remove any solids. A bright yellow clear solution is obtained. This solution of crude 10-camphorquinone sulfonyl chloride is added into an ice-cooled, rapidly stirred mixture of diethanolamine (58.4 g) and dichloromethane (50 mL) over 30 minutes. The reaction mixture is then allowed to stir for 16 h at ambient temperature. The near complete conversion of the 10-camphorquinone sulfonyl chloride is confirmed by TLC. The reaction mixture is partitioned between dichlormethane and water/NaCl. The organic phase was separated, dried and evaporated to dryness. Purification by column chromatography provided the desired product as a viscous yellow oil (6.1 g; 15%).

The invention claimed is:

1. A photoinitiator of the formula (I)

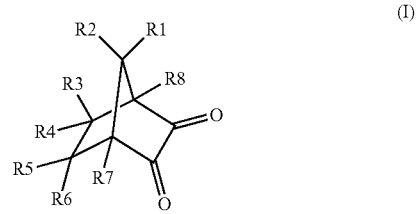

in which R3, R4, R5 and R6 are selected from H or $C_1$-$C_6$ alkyl;

wherein one of R1, R2, R7 or R8 has a structure of formula (Ia):

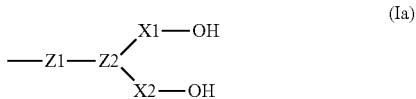

in which:

Z1 is a linker comprising one or more linker units selected from a single bond, —O—, —S—, optionally-substituted —($C_1$-$C_{12}$ alkylene)-, optionally-substituted —($C_2$-$C_{12}$ alkenylene)-, —$SO_2$—, —CO—, —NR'—, —Si(R')$_2$—, optionally-substituted heterocyclyl and optionally-substituted aryl in which R' is H or $C_1$-$C_6$ alkyl;

wherein linker —Z1-, optionally in combination with —Z2-, comprises at least one sulfonamide, a sulfonic ester, a carboxamide or a carboxylate ester moiety;

Z2 is a trivalent nitrogen atom or Z2 is C(R"), in which R" is H or $C_1$-$C_6$ alkyl; provided that—when Z2 is a nitrogen atom—the linker unit in Z1 adjacent to Z2 is —$SO_2$— or —CO—;

each of X1 and X2 are independently selected from a single bond, or a linker comprising one or more linker units selected from —O—, —S—, optionally-substituted —($C_1$-$C_{12}$ alkylene)-, optionally-substituted —($C_2$-$C_{12}$ alkenylene)-, —$SO_2$—, —CO—, —NR'—, optionally-substituted heterocyclyl and optionally-substituted aryl in which R' is H or $C_1$-$C_6$ alkyl;

and wherein X1 and X2 may be linked to one another or to Z1 to form one or more ring structures; and wherein the remaining R1, R2, R7 and R8 are selected from H or $C_1$-$C_6$ alkyl.

2. The photoinitiator according to claim 1, wherein one of R2, R7 or R8, has a structure of formula (Ia).

3. The photoinitiator according to claim 1, wherein R3, R4, R5 and R6 are H or methyl.

4. The photoinitiator according to claim 3, wherein each R3, R4, R5 and R6 is a H.

5. The photoinitiator according to claim 1, wherein R1 and R2 are both methyl.

6. The photoinitiator according to claim 1, wherein at least one linker unit in Z1 is selected from —SO$_2$—, —O— or —CO—.

7. The photoinitiator according to claim 6, wherein the at least one linker unit in Z1 is-SO$_2$— or —CO—.

8. The photoinitiator according to claim 1, wherein —Z1-Z2- has a structure selected from —SO$_2$—N—; —CO—N—; —CO—O—CR"—; —O—CO—CR"—; alkylene)-SO$_2$—N—; —(C$_1$-C$_{12}$ alkylene)-CO—N—; —(C$_1$-C$_{12}$ alkylene)-CO—O—CR"—; alkylene)-O—CO—CR"—, alkylene)-SO$_2$—O—(C$_1$-C$_{12}$ alkylene)-Z2-; —(C$_1$-C$_{12}$ alkylene)-SO$_2$—NR'—(C$_1$-C$_{12}$ alkylene)-Z2-; —(C$_1$-C$_{12}$ alkylene)-O—SO$_2$—(C$_1$-C$_{12}$ alkylene)-Z2-; —(C$_1$-C$_{12}$ alkylene)-NR'—SO$_2$—(C$_1$-C$_{12}$ alkylene)-Z2-; —(C$_1$-C$_{12}$ alkylene)-CO—O—(C$_1$-C$_{12}$ alkylene)-Z2-; —(C$_1$-C$_{12}$ alkylene)-O—CO—(C$_1$-C$_{12}$ alkylene)-Z2-; —(C$_1$-C$_{12}$ alkylene)-CO—NR'—(C$_1$-C$_{12}$ alkylene)-Z2-; or —(C$_1$-C$_{12}$ alkylene)-NR'—CO—(C$_1$-C$_{12}$ alkylene)-Z2.

9. The photoinitiator according to claim 1, wherein —Z1-Z2- has a structure selected from —SO$_2$—N—; —CO—N—; —CO—O—CR"—; —O—CO—CR"; —(C$_1$-C$_{12}$ alkylene)-SO$_2$—N—; —(C$_1$-C$_{12}$ alkylene)-CO—N—; —(C$_1$-C$_{12}$ alkylene)-CO—O—CR"—; alkylene)-O—CO—CR"—; alkylene)-SO$_2$—O—(C$_1$-C$_{12}$ alkylene)-Z2-; —(C$_1$-C$_{12}$ alkylene)-SO$_2$—NR'—(C$_1$-C$_{12}$ alkylene)-Z2-; —(C$_1$-C$_{12}$ alkylene)-CO—O—(C$_1$-C$_{12}$ alkylene)-Z2-; or —(C$_1$-C$_{12}$ alkylene)-CO—NR'—(C$_1$-C$_{12}$ alkylene)-Z2-.

10. The photoinitiator according to claim 1, wherein —Z1-Z2- has a structure selected from —SO$_2$—N—; —CO—N—; —(C$_1$-C$_{12}$ alkylene)-SO$_2$—N—; —(C$_1$-C$_{12}$ alkylene)-CO—N—; —(C$_1$-C$_{12}$ alkylene)-SO$_2$—O—(C$_1$-C$_{12}$ alkylene)-Z2-; or —(C$_1$-C$_{12}$ alkylene)-CO—O—(C$_1$-C$_{12}$ alkylene)-Z2-.

11. The photoinitiator according to claim 1, wherein Z2 is N.

12. The photoinitiator according to claim 1, wherein Z2 is C(R"), wherein R" is H, methyl, ethyl or propyl.

13. The photoinitiator according to claim 1, wherein the —(C$_1$-C$_{12}$ alkylene)- linker unit in Z1 is a —(C$_1$-C$_6$ alkylene)-.

14. The photoinitiator according to claim 13, wherein the —(C$_1$-C$_6$ alkylene)- linker unit in Z1 is propylene, ethylene or methylene.

15. The photoinitiator according to claim 1, wherein X1 and X2 are each independently selected from —O—, —S—, optionally-substituted —(C$_1$-C$_{12}$ alkylene)-, —SO$_2$—, —CO—, and —NR'— in which R' is H or C$_1$-C$_6$ alkyl.

16. The photoinitiator according to claim 15, wherein X1 and X2 are each independently selected from —O—, —S—, or an optionally-substituted —(C$_1$-C$_{12}$ alkylene)-.

17. The photoinitiator according to claim 1, wherein the —(C$_1$-C$_{12}$ alkylene)- linker unit in X1 and X2 is a —(C$_1$-C$_6$ alkylene)-.

18. The photoinitiator according to claim 17, wherein the —(C$_1$-C$_6$ alkylene)- linker unit in X1 and X2 is a propylene, ethylene or methylene.

19. The photoinitiator according to claim 1, wherein X1 and X2 are the same.

20. The photoinitiator according to claim 1, wherein one of R1, R2, R7 or R8 is selected from:

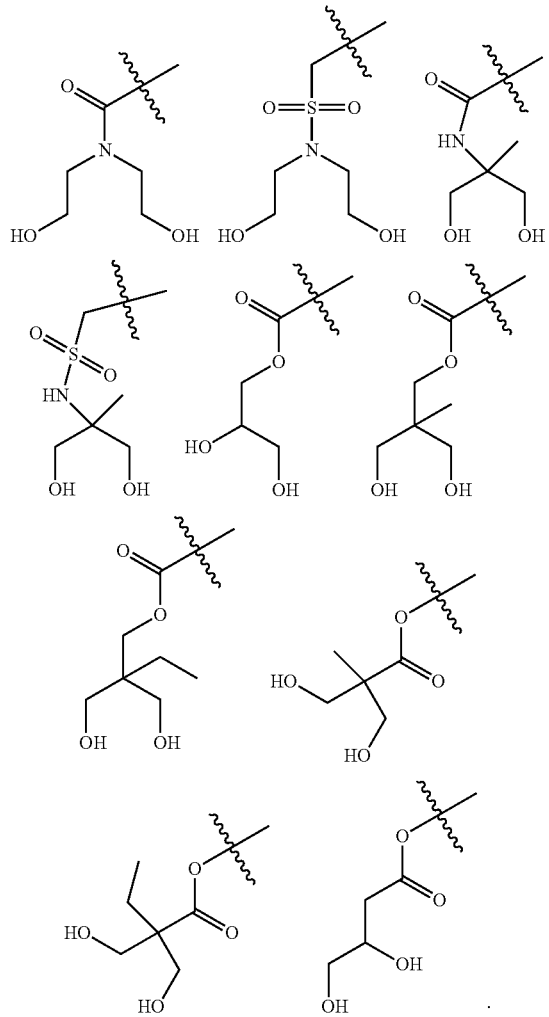

21. The photoinitiator according to claim 1, selected from:

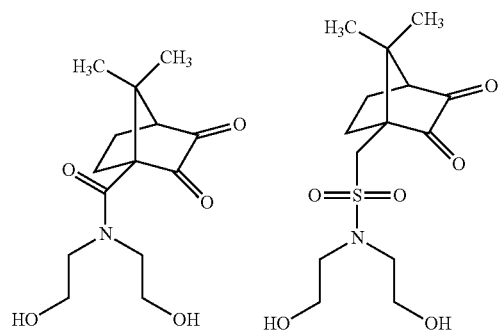

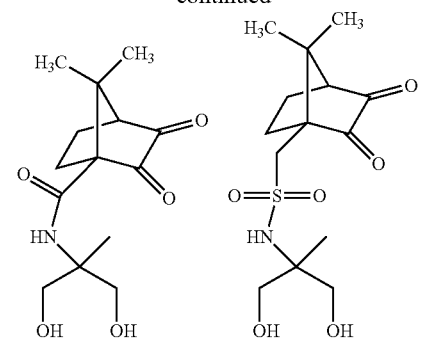
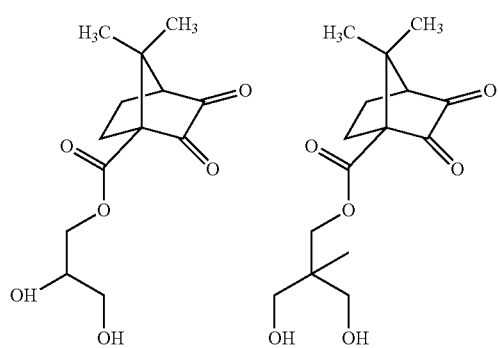
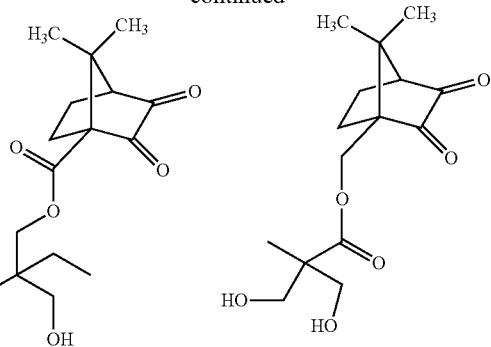
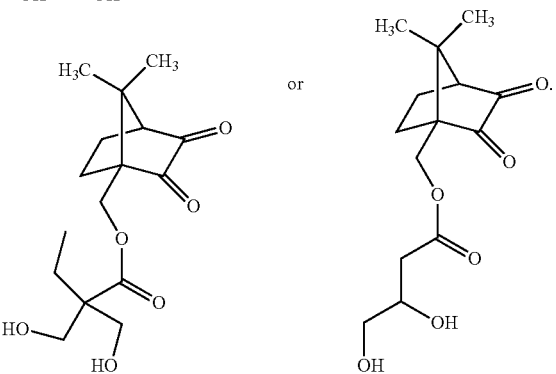
* * * * *

UNITED STATES PATENT AND TRADEMARK OFFICE
CERTIFICATE OF CORRECTION

Page 1 of 2

PATENT NO. : 10,696,626 B2
APPLICATION NO. : 16/462940
DATED : June 30, 2020
INVENTOR(S) : Fristrup et al.

It is certified that error appears in the above-identified patent and that said Letters Patent is hereby corrected as shown below:

On the Title Page

In item (54), in Title, in Column 1, Line 1, delete "PHOTOINITATORS" and insert -- PHOTOINITIATORS --, therefor.

In item (56), under "OTHER PUBLICATIONS", in Column 2, Line 1, delete "et al." and insert -- et al., --, therefor.

In item (56), under "OTHER PUBLICATIONS", in Column 2, Line 5, delete "et al.." and insert -- et al., --, therefor.

In item (56), under "OTHER PUBLICATIONS", in Column 2, Line 9, delete "et al.." and insert -- et al., --, therefor.

In the Specification

In Column 1, Line 1, delete "PHOTOINITATORS" and insert -- PHOTOINITIATORS --, therefor.

In Column 4, Line 22, delete "—CR"—," and insert -- —CR"—; --, therefor.

In Column 8, Lines 47-53, delete " 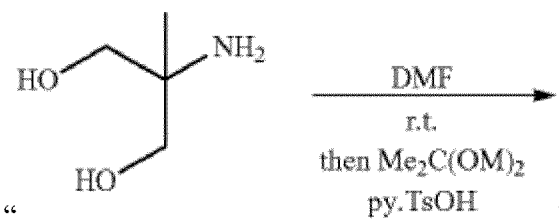 " and insert

Signed and Sealed this
Twenty-ninth Day of December, 2020

Andrei Iancu
*Director of the United States Patent and Trademark Office*

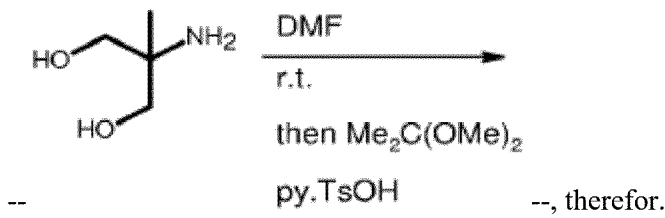 --, therefor.

In the Claims

In Column 13, Line 16, in Claim 8, delete "alkylene)-" and insert -- -($C_1$-$C_{12}$ alkylene)- --, therefor.

In Column 13, Line 19, in Claim 8, delete "alkylene)-O—CO—CR"—," and insert -- -($C_1$-$C_{12}$ alkylene)-O—CO—CR"—; --, therefor.

In Column 13, Line 20, in Claim 8, delete "alkylene)-$SO_2$—" and insert -- -($C_1$-$C_{12}$ alkylene)-$SO_2$— --, therefor.

In Column 13, Line 34, in Claim 9, delete "alkylene)-O—" and insert -- -($C_1$-$C_{12}$ alkylene)-O— --, therefor.

In Column 13, Line 35, in Claim 9, delete "alkylene)-$SO_2$—" and insert -- -($C_1$-$C_{12}$ alkylene)-$SO_2$— --, therefor.